United States Patent [19]  [11] 4,093,608
Iga et al.  [45] June 6, 1978

[54] PROCESS FOR PURIFYING COAGULATION FACTOR VIII USING DEAE-CROSSLINKED DEXTRAN

[75] Inventors: Yoshiro Iga, Nishinomiya; Masashi Shiga, Nagaokakyo, both of Japan

[73] Assignee: The Green Cross Corporation, Osaka, Japan

[21] Appl. No.: 783,625

[22] Filed: Apr. 1, 1977

[30] Foreign Application Priority Data

Apr. 9, 1976 Japan .................................. 51-39894

[51] Int. Cl.$^2$ .............................................. C07G 7/00
[52] U.S. Cl. ................................ 260/112 B; 424/101; 424/177
[58] Field of Search ..................... 260/112 B; 424/101, 424/177

[56] References Cited

U.S. PATENT DOCUMENTS

| | | | |
|---|---|---|---|
| 3,717,708 | 2/1973 | Wada et al. | 260/112 B X |
| 3,803,115 | 4/1974 | Fekete et al. | 260/112 B |
| 3,920,625 | 11/1975 | Andersson et al. | 424/101 X |

OTHER PUBLICATIONS

New England J. of Med. 280, 581–586 (1969), Hoag et al.
Proc. Soc. Expgl. Biol. Med. 116(1), 120–122 (1964), Lewis.
Chem. Abstracts, vol. 63, 1965, 4099d–e, Michael et al.
British J. Haematology, 1963, 9, pp. 236–244, Michael et al.
Pathol.-Biol. 1975, 23, Suppl, 11–16 (Mazurier et al.).

*Primary Examiner*—Howard E. Schain
*Attorney, Agent, or Firm*—Cushman, Darby & Cushman

[57] ABSTRACT

A process for purifying coagulation factor VIII which comprises contacting a plasma or a plasma fraction containing prothrombin complex and coagulation factor VIII (antihemophilic factor A) with diethylaminoethyl-crosslinked dextran to adsorb and remove the prothrombin complex from said plasma or plasma fraction. Coagulation factor VIII thus obtained can be administered to control the bleeding in hemophilia A patients.

1 Claim, 2 Drawing Figures

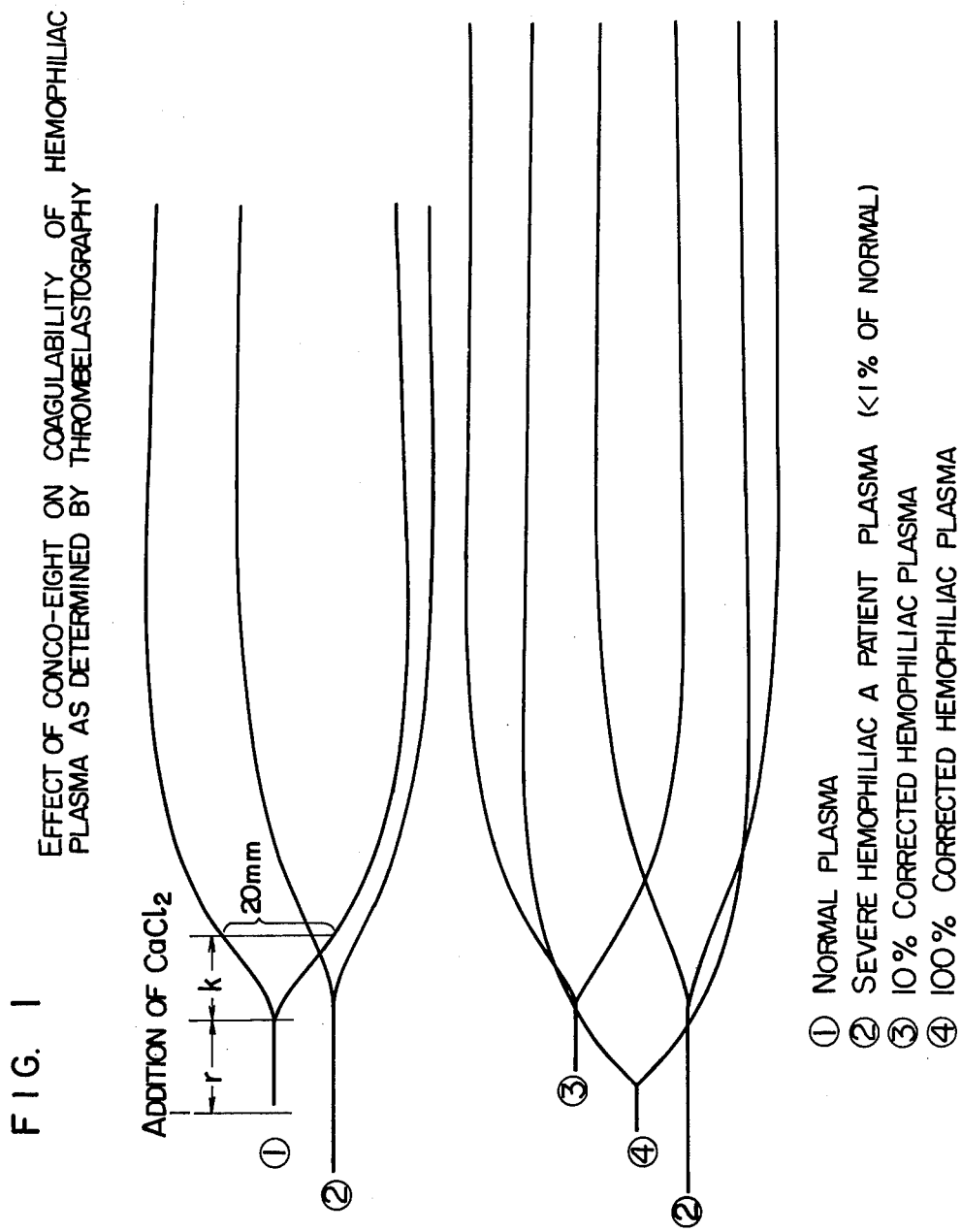

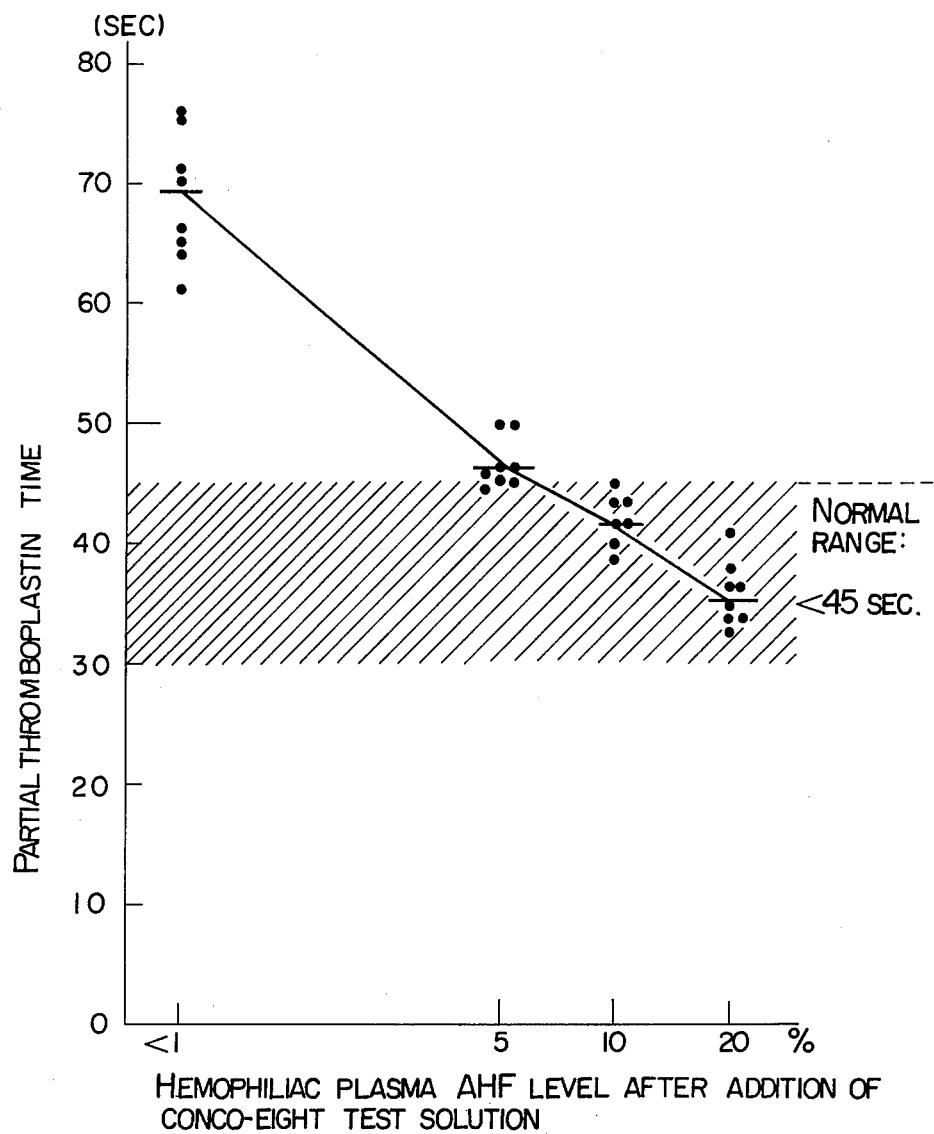

PROCESS FOR PURIFYING COAGULATION FACTOR VIII USING DEAE-CROSSLINKED DEXTRAN

This invention relates to a process for separating coagulation factor VIII (hereinafter referred to as "factor VIII") from human fresh pooled plasma and purifying it. More particularly, this invention relates to a process for separating and purifying factor VIII characterized by absorbing and removing prothrombin complex, the instabilization factor for factor VIII, from human pooled plasma containing factor VIII or factor VIII fractions thereof by the use of diethylaminoethyl-crosslinked dextran.

The accompanying drawings illustrate the effect of the factor VIII preparation obtained according to the process of this invention, wherein FIG. 1 shows an effect on coagulability of hemophilic plasma as determined by thrombelastography.

FIG. 2 shows an effect on coagulability of hemophilic plasma as determined by the partial thromboplastin time.

Factor VIII has another name of anti-hemophilic factor A. It is one of the most important coagulation factors participating into the intrinsic thromboplastin generation. When attempting to treat hemorrhage of a hemophiliac patient, the most rational and effective method is to directly introduce the deficient factor, namely factor VIII, into the bloodstream. However, factor VIII is quite difficult to separate and purify because of its low content in the plasma and the instableness of its activity. At the present time, a few kinds of factor VIII preparations are commercially available and extensively used for the treatment of hemophiliac A patients. They are prepared from the fraction I separated from plasma by means of Cohn's ethanol fractionation method or from the cryoprecipitate obtained by freezing a plasma and then thawing it at a low temperature. However, they are all crude products of low purity and contain a large quantity of fibrinogen. If given at a large or frequently repeated dose, they may make the state of patient quite danger clinically, bringing an excessively overloading fibrinogen in the circulating system. Moreover, it is difficult to determine their accurate dose because of the deviation in the activity in each preparation. For the above-mentioned reasons, the current trend in the world is towards the development of a highly purified, highly concentrated factor VIII preparation from a large quantity of pooled plasma. The high potency factor VIII concentrates hitherto disclosed are generally produced by once preparing crude fractions of factor VIII, such as Cohn's fraction I or cryoprecipitate, followed by purifying them by the method of polyethylene glycol fractionation or glycine-precipitated fractionation. Partial improvements of these processes are disclosed in U.S. Pat. Nos. 3,631,018 and 3,652,530.

As Kisker [Thromb. Diath. Haemorrhagica, 17, 381 (1967)], as well as Penick and Brinkhouse [Amer. J. Med. Sciences, 232, 434 (1956)], have pointed out in their papers, in the preparative process of such high potency factor VIII concentrates, particularly in the course of separating and purifying factor VIII, the coexisting prothrombin complex and active forms of its constitutive factors, such as IIa, Xa and the like, are markedly detrimental to the stability of factor VIII and sometimes irreversibly injure the latter to inactivate it. In order to improve stability, yield and solubility of factor VIII, therefore, it is quite important and essentially necessary to inactivate or eliminate said instabilization factors at the earliest stage of the separation-purification step. Method for inactivating said instabilization factors has been disclosed in, for example, U.S. Pat. No. 3,803,115. It has also been disclosed that said instabilization factors can be removed by the use of an adsorbent such as aluminum hydroxide, magnesium hydroxide, barium carbonate, barium sulfate, rivanol (6,9-diamino-2-ethoxyacridine lactate), ion-exchange resin (Amberlite IRC-50), glycine ethyl ester or the like [Bidwell, E. et al.: Brit. J. Haemat., 13, 568 (1967); Soulier, J. P. et al.: Presse med., 72, 1223 (1964); Surgenor, P. M. et al.: J. Phys. Colloid Chem., 55, 94 (1951); Hoag, M. S. et al.: J. Clin. Invest., 39, 554 (1960)]. Among them, aluminum hydroxide is known to be relatively good adsorbent of said instabilization factors and therefore has been used most frequently. However, aluminum hydroxide is still disadvantageous in the following respects: (1) it cannot be said to be satisfactory in the removal rate of said instabilization factors, particularly of prothrombin complex, and it can exercise an undesirable effect upon the stability or some other properties of factor VIII; (2) it reacts with citric acid (or its salts) to form a gel, so that its use precludes the possibility of employing citric acid salt as an effective solubilizing and stabilizing composition for factor VIII throughout the fractionation process of the latter; and (3) after the treatment with aluminum hydroxide, there remains a small quantity of aluminum ion ($Al^{+++}$) capable of reacting with the subsequently added citric acid salt to form a small quantity of gel, which causes clogging of the membrane filter, makes the procedure of steril-filtration quite difficult, and thereby causes a great loss in factor VIII. As above, the treatment with aluminum hydroxide can profoundly affect the stability, yield and solubility of factor VIII as well as the procedure for separating and purifying it. Solution of these problems, therefore, has a deep significance in the production of high potency factor VIII concentrates.

In view of above, the inventors tentatively applied various adsorbents substitutive for aluminum hydroxide to the separation and purification of factor VIII with the aim of overcoming the above-mentioned difficulties encountered in the treatment with aluminum hydroxide. As the result, it was found that only prothrombin complex can be removed from a solution containing both factor VIII and prothrombin complex with a high efficiency if diethylaminoethyl-crosslinked dextran is used as an adsorbent under appropriate conditions.

M. S. Hoag et al. [New Eng. J. Med., 280, 581 (1969)] have stated in their paper that diethylaminoethyl crosslinked dextran can function as an adsorbent of prothrombin complex. On the other hand, S. E. Michael and G. W. Tunnah [British J. Haemat., 9, 236–244 (1963)] have stated in their paper that diethylaminoethyl-crosslinked dextran can function as an adsorbent of factor VIII. Thus it is natural to consider that when used as an adsorbent in the purification of factor VIII contaminated by prothrombin complex, diethylaminoethyl-crosslinked dextran will adsorb not only prothrombin complex but also factor VIII to reduce the yield of factor VIII greatly. This is the reason why diethylaminoethyl-crosslinked dextran has never been used for separating factor VIII from prothrombin complex hitherto. Nevertheless, the study of the present inventors has revealed a difference between factor VIII and prothrombin complex in the adsorption behavior to diethylaminoethyl-crosslinked dextran. Thus, the inventors have succeeded in discovering the conditions under which prothrombin complex is almost exhaustively adsorbed whereas factor VIII is hardly adsorbed. Based on this finding, the present invention has been accomplished.

Thus, it is an object of this invention to provide a novel process for separating and purifying factor VIII from human pooled plasma.

It is a further object of this invention to provide a process for the removal of prothrombin complex, responsible for the degradation or inactivation of factor VIII, from human pooled plasma.

It is another object of this invention to obtain coagulation factor VIII from human pooled plasma in a high yield.

It is yet another object of this invention to provide a process for improving stability and solubility of factor VIII.

Other objects and advantages of this invention will become apparent from the descriptions given below.

According to this invention, there is provided a process for purifying factor VIII which comprises contacting a plasma or a plasma fraction containing both prothrombin complex and factor VIII with 0.5 to 3 mg (dry weight) of diethylaminoethyl-crosslinked dextran per one unit of prothrombin, thereby adsorbing the prothrombin complex to said diethylaminoethyl-crosslinked dextran and removing the prothrombin complex.

Diethylaminoethyl-crosslinked dextran used in this invention is manufactured as the registered tradename "DEAE-Sephadex ®" by Pharmacia Fine Chemicals Co., Sweden. It includes two types of products, Sephadex ® A-50 and Sephadex ® A-25, different from each other in the degree of crosslinkage. Any of the two types may be used in this invention.

In this invention, the object from which prothrombin complex is to be removed upon the treatment with diethylaminoethyl-crosslinked dextran is a plasma or a plasma fraction containing factor VIII and prothrombin complex. The treatment with diethylaminoethyl-crosslinked dextran is expectable to be more effective when the said object is in a less purified state with respect to factor VIII. Although the adsorption of prothrombin complex is not affected by the purity of factor VIII present in plasma or plasma fraction and a high rate of removal is attainable at any stage of purification, the adsorbed loss of factor VIII increases with purity of factor VIII present in the object. Therefore, the treatment with diethylaminoethyl-crosslinked dextran can be more effective when carried out in the earlier stage of purification. Thus, it can be most effective when a plasma is directly treated with diethylaminoethyl-crosslinked dextran. In the treatment, diethylaminoethyl-crosslinked dextran is preferably used in an amount of 0.5 to 3 mg, particularly 1.0 to 1.5 mg, (dry weight) per one unit of prothrombin present in plasma or factor VIII fraction. If the quantity of diethylaminoethyl-crosslinked dextran exceeds the said range, the adsorption of prothrombin complex cannot take place efficiently or there occurs a loss in factor VIII. It is a matter of course that diethylaminoethyl-crosslinked dextran should be swollen, buffered and steam-sterilized at 121° C for 30 min. before use. The plasma or factor VIII fraction to be contacted with diethylaminoethyl-crosslinked dextran preferably has a pH value of 6.8 to 7.9 and a temperature of 0° to 10° C. If its pH is out of this range, factor VIII and prothrombin complex become susceptible to inactivation. Preferably, it has an electric-conductivity of 7,000 to 12,000 $\mu$ U/cm as measured with Degital Conduct Meter model CM-15A (manufactured by TOA Electronics LTD). A contact time of 10 to 60 minutes is usually enough to complete the treatment. Among the above-mentioned conditions, a particular importance is attached to electric-conductivity. It should be in the range of 7,000 to 12,000 $\mu$ U/cm, particularly 8,500 to 9,500 $\mu$ U/cm. If it exceeds 12,000 $\mu$ U/cm, adsorption and removal of prothrombin complex becomes insufficient. If it is less than 7,000 $\mu$ U/cm, there occurs a partial adsorption of factor VIII to cause its loss. After prothrombin complex has been removed under the above-mentioned conditions, the remaining plasma or plasma fraction containing factor VIII may additionally be purified, if necessary, in the usual manner by isolating cryo-ethanol precipitate according to the Cohn's Ethanol Fractionation method [Blombäck, Arkiv For Kemi, Bd. 12, Nr. 36, 387–396 (1958)] followed by refining the precipitate with polyethylene glycol [Polson, Vox Sang, 23, 107–118 (1972)] and/or glycine [Hurt, Thromb. Diath. Haemorr., 15, 327–337 (1966)].

Thus, a pooled plasma is preliminarily adjusted to a pH value of 6.8 to 7.9 and an electric-conductivity of 7,000 to 12,000 $\mu$ U/cm and then contacted with 0.3 – 5 mg (dry weight) of DEAE-Sephadex ® A-50 gel per one ml of the plasma at a liquid temperature of 0° to 10° C for about 30 minutes with stirring until prothrombin complex has been adsorbed to DEAE-Sephadex. Then, the DEAE-Sephadex is centrifuged off, and there is obtained a deprothrombinized plasma as a supernatant. Subsequently, 53% (V/V) ethanol is added to the latter at −1° to −4° C until the final concentration of ethanol has reached 3 to 8% (V/V), whereby a cryo-ethanol precipitate is obtained. At this stage, the yield of factor VIII is 72.7 to 88.3% and its specific activity (factor VIII unit/A 280) is 18.3 to 29.6 times, based on the source plasma. The above-mentioned values are much superior to those reported in the past, because they are not the values given by a conventional cryo-precipitate prepared by a mere cooling but the values given by a deprothrombinized factor VIII fraction. In the next stage, the cryo-ethanol precipitate is dissolved into an appropriate medium such as tris-citrate buffer (pH 7.0–7.4), 3 to 5% (W/V) of polyethylene glycol (molecular weight: 4,000) is added according to the method of Polson et al. to remove fibrinogen as a precipitate, and the supernatant factor VIII fraction is concentrated with polyethylene glycol (molecular weight: 4,000) and/or glycine to give a purified factor VIII paste. Conco-eight (trade-name of a product manufactured by The Green Cross Corp.) is a stable, dried product of human antihemophilic factor (factor VIII) in concentrated form, prepared from the highly purified factor VIII paste. Table 1 shows the potencies and properties of Conco-eight and three other products A, B and C made by other companies.

Table 1

| | Comparison between Conco-eight and other products in potency and properties | | | |
|---|---|---|---|---|
| Properties | Conco-eight (500 u/20 ml) | Product: A (290 u/10 ml) | Product: B (260 u/10 ml) | Product: C (250 u/10 ml) |
| Solubility at 30° – 37° C (min) | <10 | 15 | 20 | <10 |
| Property when dissolved | | Slightly white liquid | | Pale Yellow liquid |
| Factor VIII Potency (unit/ml) | 25.0 | 25.5 | 26.1 | 25.1 |
| Protein content: | | | | |
|   Lowry-Folin (mg/ml) | 13.3 | 29.9 | 27.7 | 39.5 |
| Specific Activity (u/mg pr.) | 1.880 | 0.853 | 0.942 | 0.635 |
| Fibrinogen content (mg/ml) | 1.13 | 3.70 | 10.85 | 13.90 |
|   (mg/mg pr.) | 0.085 | 0.124 | 0.392 | 0.352 |
| Electrophoretic components (%) | | | | |
|   Albumin | 0 | 0 | 0 | 30.1 |
|   $\alpha_1$-globulin | 2.3 | 1.2 | 1.1 | 2.0 |
|   $\alpha_2$-globulin | 11.4 | 3.3 | 2.0 | 9.8 |
|   $\beta$-globulin | 11.1 | 57.2 | 42.5 | 3.8 |
|   Fibrinogen | 18.6 | 33.7 | 49.5 | 45.5 |
|   $\gamma$-globulin | 55.6 | 4.6 | 4.9 | 8.8 |
| Polyethyleneglycol content (mg/ml) | 0.32 | <0.01 | 0.54 | <0.01 |
| Isoagglutinin (reciprocal titer) | | | | |
|   Anti-A | x32 – x64 | x64 | x32 –x64 | x64 – x128 |
|   Anti-B | x32 – x64 | x64 | x32 – x64 | x64 – x128 |
| HBs-Antigen (HAI titer) | Not detected | Not detected | Not detected | Not detected |
| Anti-HBs (PHA titer) | Not detected | Not detected | Not detected | Not detected |
| Coagulation Factors | | | | |
|   Factor I | 1.13 mg/ml | 3.70 mg/ml | 10.85 mg/ml | 13.90 mg/ml |
|   Factor II | 0.035 u/ml | 0.09 u/ml | 0.026 u/ml | 0.024 u/ml |
|   Factor IIa | >24 hrs | >24 hrs | >24 hrs | >24 hrs |
|   Factor V | 0.031 u/ml | 0.06 u/ml | 0.04 u/ml | 0.152 u/ml |
|   Factor VII | 0.071 u/ml | 0.02 u/ml | 0.02 u/ml | 0.114 u/ml |
|   Factor VIII | 25.0 u/ml | 25.5 u/ml | 26.0 u/ml | 25.1 u/ml |
|   Factor IX | 0.232 u/ml | 0.95 u/ml | 0.345 u/ml | 0.45 u/ml |
|   Factor X | 0.016 u/ml | 0.013 u/ml | 0.010 u/ml | 0.101 u/ml |

Test Method
Factor I: Thrombin Clotting Time
Factor II, V, VII and X : Prothrombin Time
Factor IIa : 1% Fibrinogen Clotting Time
Factor VIII and IX : Modified Partial Thromboplastin Time Conco-eight obtained according to the process of this invention is much superior to the products of other companies in having the following excellent characteristic properties of factor VIII concentrate:

1. reconstitution is rapid and easy;
2. specific activity is high;
3. fibrinogen content is very low; and
4. prothrombin complex content is low.

FIGS. 1 and 2 illustrate the results of a in vitro test on the replacement effect of the preparation of this invention upon a plasma deficient in factor VIII.

FIG. 1 shows an effect of Conco-eight on coagulability of hemophilic plasma as determined by thrombelastography. In FIG. 1, test No. 1 shows a normal pattern, and No. 2 the pattern of severe hemophilia A patient, whose plasma was deficient in factor VIII only, the content being less than 1% of the normal value. After an administration of Conco-eight sufficient to give a 10% correction of the hemophilic character, considerable improvement was seen on the thrombelastogram, as shown in test No. 3, while when Conco-eight was administered to give a 100% correction, the thrombelastogram was rectified to the perfect pattern shown here in No. 4.

FIG. 2 shows an effect of Conco-eight on coagulability of hemophilic plasma as determined by the partial thromboplastin time (PTT). When the factor VIII level in hemophiliac plasma increased to within 5% of the normal, three of eight cases were within normal range, and if raised to the 10% level, all were involved in the normal range.

As above, the thrombelastographic finding and the partial thromboplastin time were markedly improved by the use of the preparation of this invention.

As will be understood from the descriptions given above, it is the object of this invention to provide a process for purifying factor VIII which comprises contacting a human plasma or factor VIII fractions thereof containing both factor VIII and prothrombin complex with diethylaminoethyl-crosslinked dextran to adsorb the prothrombin complex and remove it from the plasma or the fractions and then producing a factor VIII concentrate from the adsorbed supernatant. This invention has the following effects and characteristic features:

(1) Owing to the use of diethylaminoethyl-crosslinked dextran, the removal rate of prothrombin complex is 95% or more, which is far higher than the removal rate realizable in the treatment with aluminum hydroxide (80%).

(2) Throughout the treatment with diethylaminoethyl-crosslinked dextran, the loss in factor VIII is 10 to 15% when the starting material is plasma, Cohn's fraction I or cryoprecipitate. This value of loss is comparable to or less than the loss occurring in the treatment with aluminum hydroxide (8 to 22%).

(3) When plasma, as a starting material, is treated with diethylaminoethyl-crosslinked dextran, prothrombin complex is removed before the separation of factor VIII. This is quite effective in improving the stability and yield of factor VIII.

(4) Dissimilarly to aluminum hydroxide, diethylaminoethyl-crosslinked dextran forms no gel with citric acid or citrate. This enables to use citrate buffer, having a high extracting efficiency, in the extraction of factor VIII from Cohn's fraction I or cryo-precipitate, which leads to an increased yeild of factor VIII by about 10 to 15% in this stage of the treatment.

(5) For the same reason as above, the danger of clogging due to the gel formation is eliminated, which greatly facilitates the procedure of steril-filtration.

(6) Accordingly, the filtration causes no detectable loss in factor VIII, and the yield of factor VIII is greatly improved.

(7) After the adsorption of prothrombin complex, the latter can be eluted out of diethylaminoethyl-cross-linked dextran into fractions. This enables to practise removal and fractionation of prothrombin complex at once.

In conclusion, the treatment with diethylaminoethyl-crosslinked dextran is advantageous over the disclosed treatment with aluminum hydroxide in many respects.

Referring to the examples shown below, this invention will be illustrated more precisely. The examples should not be considered limitations upon this invention by any means.

In the examples, one unit of prothrombin is defined as the activity present in 1 ml of fresh pooled normal plasma, as measured according to the one-stage method mentioned in the paper of Koller, Loeliger and Duckert [Acta Haemat. 6., 1 (1951)]. On the other hand, one unit of factor VIII unit is defined as the activity present in 1 ml of fresh pooled normal plasma, as measured by the partial thromboplastin time method mentioned in the paper of Hardisty and Macpherson [Thromb. Diath. Haemorrh., 7, 215 (1962)]. Specific activity of factor VIII refers to a calculated activity of factor VIII present in 1 mg of protein.

EXAMPLE 1

1,300 liters of a fresh, frozen human plasma (total prothrombin activity $1.3 \times 10^6$ units, total factor VIII activity $1.3 \times 10^6$ units) was thawed and pooled, and then its temperature was adjusted to 4° C, its pH value was adjusted to 7.4 with 0.1 N NaOH and its electric conductivity was adjusted to 10,000 $\mu$ U/cm by adding 1 M aqueous solution of NaCl. It was contacted with 23.8 kg (dry weight 2 kg; 1.53 mg/one unit of prothrombin) of DEAE-Sephadex ® A-50, preliminarily swollen and buffered with 0.02 M citrate buffer (pH 7.0) and steam-sterilized, at 4° C for about 60 minutes with stirring until the prothrombin complex had been adsorbed to the DEAE-Sephadex ® A-50. The mixture of plasma and DEAE-Sephadex ® A-50 was then centrifuged with Sharpless centrifugal machine at the same temperature to give a deprothrombinized plasma. At this stage, the removal rate of prothrombin complex was 96.5% and the yield of factor VIII was 88.5%. Then, 53.0% (V/V) of ethanol was added to the deprothrombinized plasma at 0° to −2° C until the final concentration of ethanol in the plasma reached to 4.5% (V/V). Subsequently, it was centrifuged to isolate 8.3 kg of factor VIII fraction in the form of a cryo-ethanol precipitate, from which factor VIII was extracted into 150 liters of 0.02 M tris(hydroxymethyl)aminomethane-0.01 M sodium citrate buffer (pH 7.4). Thus, a crude solution of factor VIII having a specific activity of 25.4 times based on the source plasma was obtained in a yield of 75.3% based on the source plasma. Then, polyethylene glycol (molecular weight: 4,000) was added to the crude solution up to a concentration of 4% (W/V) to precipitate and reject fibrinogen. To the supernatant factor VIII fraction was added an additional quantity of polyethylene glycol (molecular weight: 4,000) until its final concentration reached 14% (W/V), whereby a purified factor VIII was obtained in the form of a paste. The purified paste thus obtained was washed with a small quantity of 1.8 M glycine solution to eliminate the slightly remaining polyethylene glycol, and then dissolved into 10 to 15 ml, per 1 g wet weight of the paste, of 0.01 M tris(hydroxymethyl)aminomethane-0.01 M sodium citrate-0.1 M sodium chloride solution (pH 7.4) to obtain a factor VIII concentrate solution containing about 30 units of factor VIII per 1 ml. It was steril-filtered, divided into portions, and finally freeze-dried to give a dry preparation of factor VIII concentrate. When the dry preparation was reconstituted with the same quantity of water as had been removed from one portion, the resulting solution had a factor VIII activity of 25–30 units per one ml. It had the following characteristics:

specific activity of factor VIII: 3 units/mg protein;
fibrinogen content: 0.048 mg/mg protein;
polyethylene glycol content: 0.2 mg/ml;
isoagglutinin reciprocal titer: 32 x;
HBs antigen and anti-HBs antibody: not detected by hemoagglutination inhibition method and passive hemoagglutination method;
active clotting factor: not less than 24 hrs. by 1% fibrinogen clotting time.

EXAMPLE 2

1,300 liters of a fresh frozen pooled human plasma was thawed and pooled, to which was added 5% (V/V) of ethanol at 0° to −2° C to isolate a fraction of factor VIII in the form of a cryo-ethanol precipitate. It was added to 130 liters of 0.02 M tris(hydroxymethyl)aminomethane-0.01 M sodium citrate solution (pH 7.0). The resulting mixture was stirred at 25° and then centrifuged to give a crude extract solution of factor VIII (total prothrombin activity 40,000 units; total factor VIII activity $1.04 \times 10^6$ units). Its temperature was adjusted to 4° C, its pH value was adjusted to 7.0 with 0.1 N hydrochloric acid, and its electric conductivity was adjusted to 9,000 $\mu$ U/cm with 1 M NaCl solution. Then, 450 g of DEAE-Sephadex ® A-25 gel (40 g in dry weight: 1 mg/one unit of prothrombin) was added to it, and they were contacted each other with stirring. The mixture was centrifuged to separate DEAE-Sephadex ® A-25 together with the adsorbed prothrombin complex, and there was obtained a crude solution of factor VIII not contaminated by prothrombin complex as the supernatant. At this stage, the yield of factor VIII was 63.5% and the purity was 19.5 times, based on the source plasma. Thereafter, fibrinogen was removed and factor VIII was concentrated according to the polyethylene glycol fractionation method by repeating the procedure of Example 1, and then the highly purified factor VIII paste thus obtained was formed into a preparation, whereby there was obtained a high potency factor VIII concentrate comparable to the preparation of Example 1 in the characteristic properties.

What is claimed is:

1. A process for purifying coagulation factor VIII which comprises contacting for 10 to 60 minutes a human plasma or plasma fraction containing both prothrombin complex and factor VIII, said plasma or plasma fraction having an electroconductivity in the range of 7,000 to 12,000 $\mu$ U/cm, a pH of 6.8 to 7.9, and a liquid temperature of 0° to 10° C, with diethylaminoethyl cross-linked dextran and thereby adsorbing and removing said prothrombin complex.

* * * * *